United States Patent [19]
Hille et al.

[11] Patent Number: 5,240,711
[45] Date of Patent: Aug. 31, 1993

[54] TRANSDERMAL THERAPEUTIC SYSTEM COMPRISING AS ACTIVE COMPONENT BUPRENORPHINE

[75] Inventors: Thomas Hille, Neuwied; Lothar Deurer, Koblenz; Hans-Rainer Hoffmann, Neuwied, all of Fed. Rep. of Germany

[73] Assignee: LTS Lohmann Therapie-Systeme GmbH & Co. KG, Neuwied, Fed. Rep. of Germany

[21] Appl. No.: 951,030

[22] Filed: Sep. 24, 1992

Related U.S. Application Data

[63] Continuation of Ser. No. 619,375, Nov. 28, 1990.

[30] Foreign Application Priority Data

Nov. 29, 1989 [DE] Fed. Rep. of Germany ....... 3939376

[51] Int. Cl.⁵ ............................................ A61F 13/02
[52] U.S. Cl. .................................. 424/448; 401/449; 401/441; 401/443
[58] Field of Search ........................ 424/447, 449, 448

[56] References Cited

U.S. PATENT DOCUMENTS

| | | | |
|---|---|---|---|
| 4,806,341 | 2/1989 | Chien et al. | 424/449 |
| 4,911,916 | 3/1990 | Cleary | 424/449 |
| 4,915,950 | 4/1990 | Miranda et al. | 424/447 |
| 4,983,395 | 1/1991 | Chang et al. | 424/449 |

Primary Examiner—Thurman K. Page
Assistant Examiner—Leon R. Horne
Attorney, Agent, or Firm—Sprung Horn Kramer & Woods

[57] ABSTRACT

The controlled release of buprenorphine or the pharmaceutically acceptable salts thereof to the skin over a period of time of at least 24 hours is ensured by a transdermal therapeutic system consisting of a backing layer which is impermeable to the active substance, a pressure-sensitive adhesive reservoir layer, and optionally a removable protective layer. Said reservoir layer of said system comprises 20 to 90%-wt polymeric material, 0.1 to 30%-wt softener, 0.1 to 20%-wt buprenorphine base or one of the pharmaceutically acceptable salts thereof, and 0.1 to 30%-wt solvent for the active substance base.

18 Claims, 3 Drawing Sheets

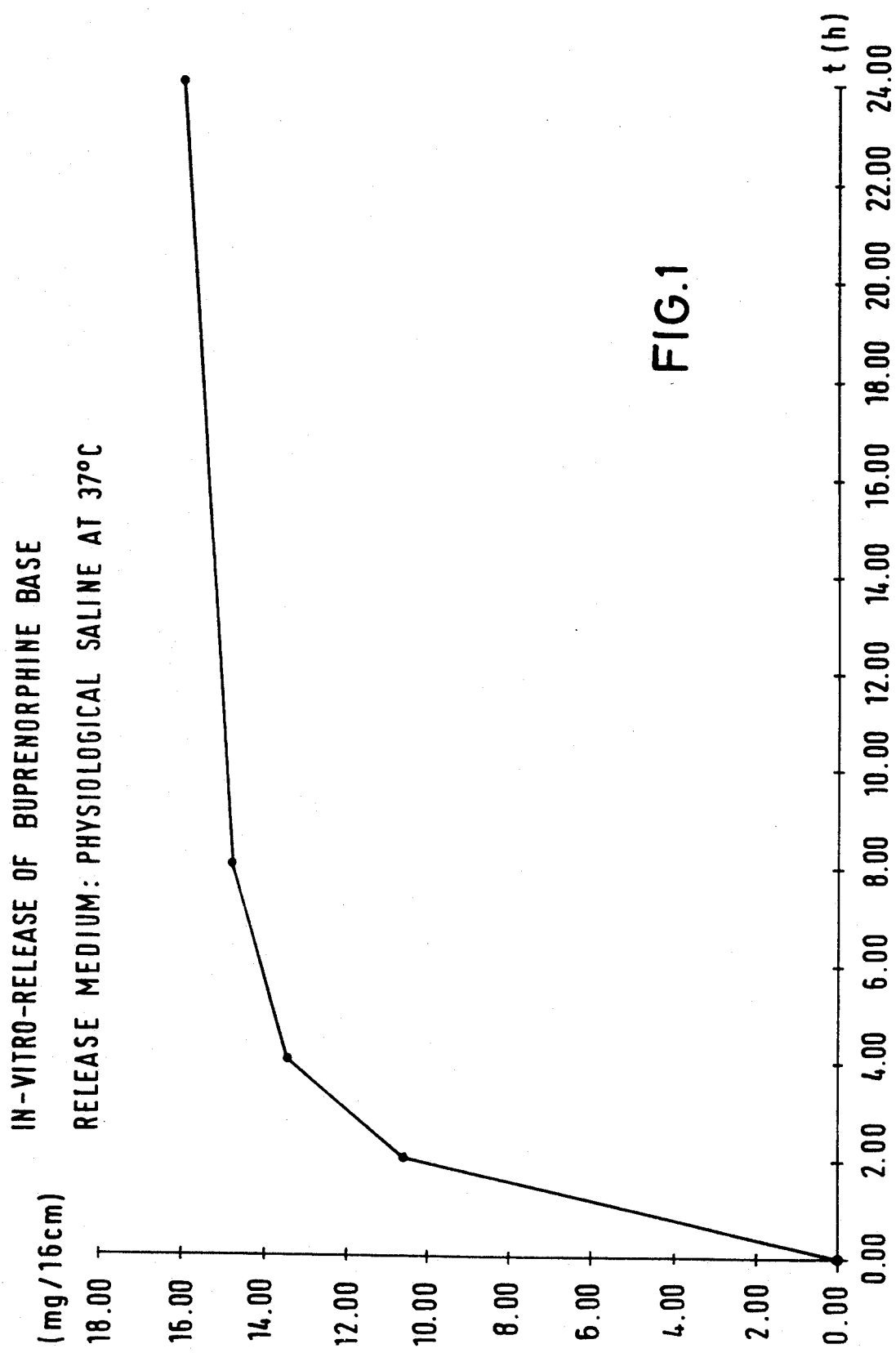

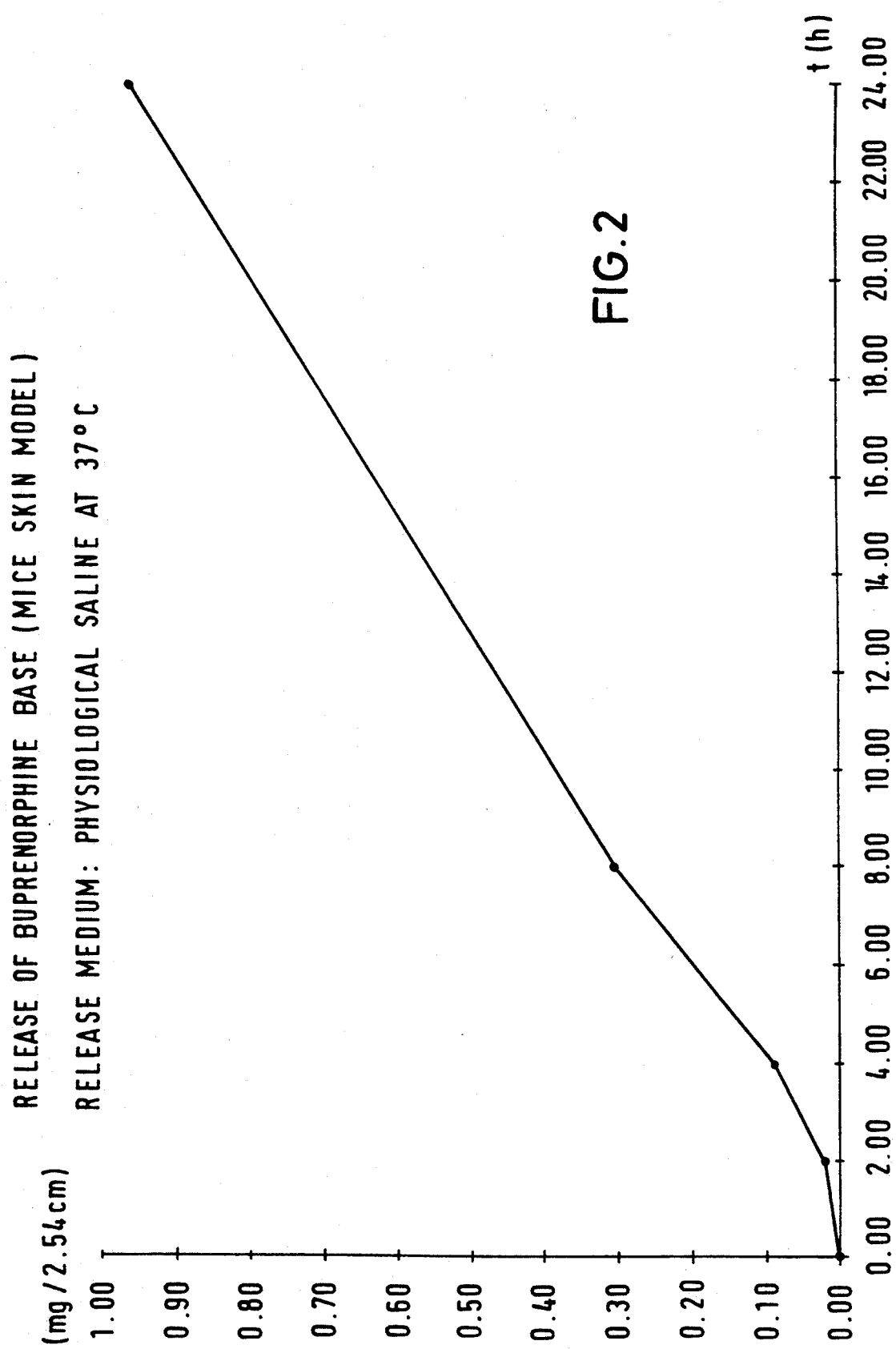

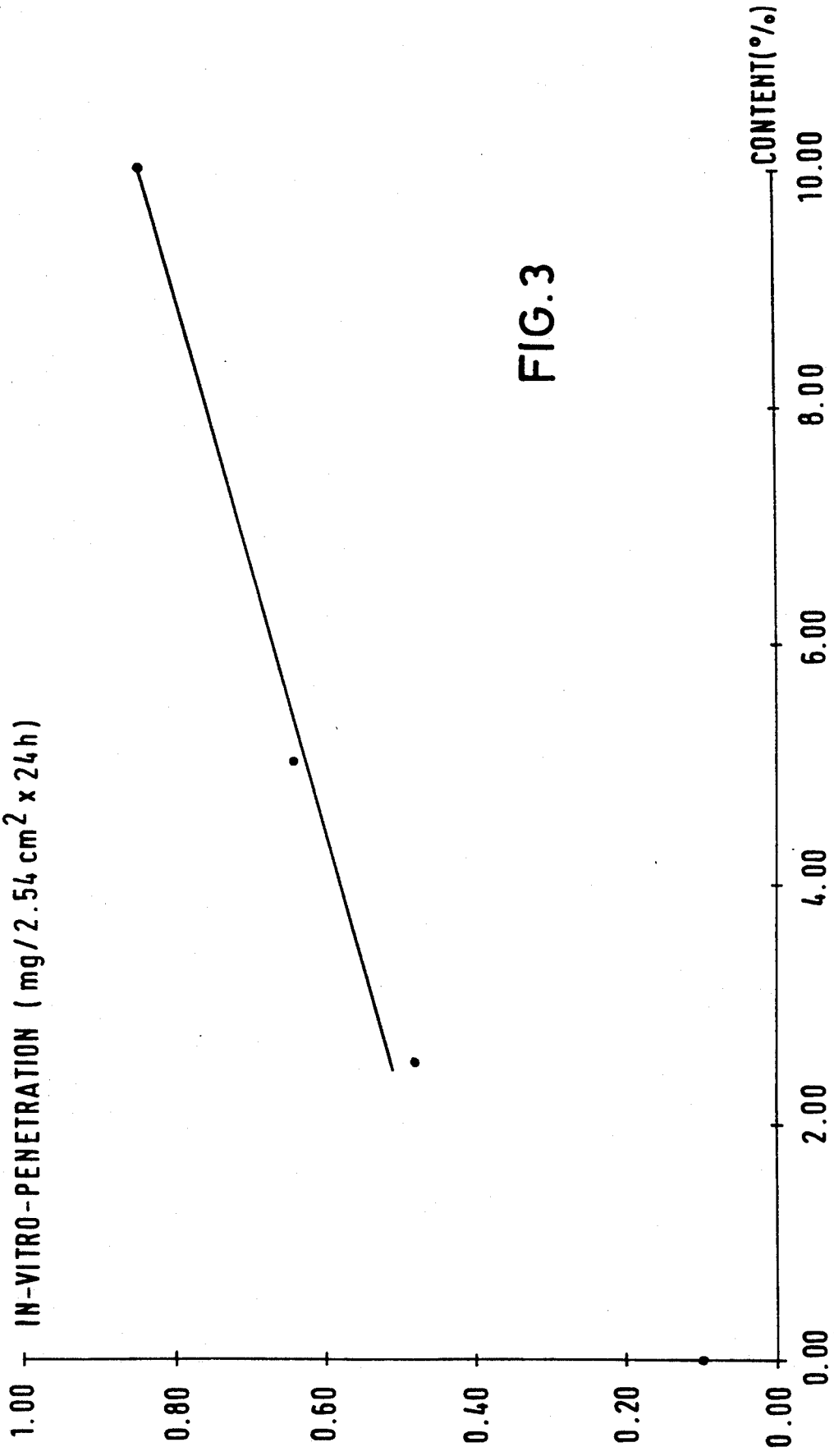

TRANSDERMAL THERAPEUTIC SYSTEM COMPRISING AS ACTIVE COMPONENT BUPRENORPHINE

This application is a continuation of application Ser. No. 619,375, filed Nov. 28, 1990.

DESCRIPTION

The present invention relates to a transdermal therapeutic system (TTS) which contains as active component buprenorphine (17-(cyclopropylmethyl)-α-(1,1-dimethylethyl)-4,5-epoxy-18,19-dihydro-3-hydroxy-6-methoxy-α-methyl-6,14-ethenomorphinane-7-methanol).

Buprenorphine is a partially synthetic opiate. Compared to other compounds of this class of substances, the advantage of buprenorphine is higher effectiveness. This means that patients suffering from cancer or a tumor with unfavorable diagnosis in final stage can be relieved from pain with daily doses of about 1 mg. However, buprenorphine does not solve two major problems occurring in connection with opiates, i.e., the danger of habit formation and the low bioavailability of these substances in case of oral administration. For example, the bioavailability from the gastrointestinal tract amounts to only about 10%, and in case of sublingual application only about 50%.

When buprenorphine was introduced as analgesic, it was regarded as non-habit-forming. However, this initial assumption has been corrected. In the meantime, buprenorphine is subject to the German narcotics act, after it had been increasingly abused by addicts.

However, since quite recently, experts are of the opinion that it is the form of administration of a medicinal drug which contributes to the risk of addiction. This can easily be understood in case of high-potency analgesics in the therapy of extreme pain.

Immediately after application the blood level of the analgesic is higher than therapeutically required and causes euphoria, however, then drastically decreases and rapidly effects blood levels which do no longer treat the pain successfully. Due to this pain, the patient starts to long for the next dosage—an iatrogenic addiction is created.

In case of buprenorphine and other highly effective opiates continuous infusion would therefore be the most suitable kind of administration to avoid said iatrogenic habit formation by means of constant blood levels. However, continuous infusion cannot be applied and controlled without any aid of a physician during domiciliary care; inflammations frequently result at the place where the cannula is inserted.

Even an oral depot preparation cannot be the suitable form to administer buprenorphine, since the low bioavailability in case of oral application requires approximately ten times the amount of active substance compared to the required intravenous dosage. In this connection, buprenorphine, as partial opiate antagonist, involves great problems, since a respiratory depression caused by an overdosage of the active substance cannot be treated by the administration of an antagonist, such as nalorphine which is the suitable antidote in case of poisonings caused by opiates. Although the oral bioavailability for buprenorphine is state to be 10%, overdosages may nevertheless occur, since buprenorphine shall also be administered to patients with the probability of liver function disturbances so that quite more than 10% of buprenorphine may survive the first liver passage without having been subjected to metabolism.

In addition, the development on the market for medicinal agents during the last years has shown that oral depot preparations are not always suitable. Generics having the same in-vitro-release as preparations of the original suppliers do not have the same effectiveness as those original preparations. This means that overdosages and underdosages may arise due to uncontrolled release in vivo. Both cases are disastrous in case of buprenorphine. In case of underdosage, the patient suffers from intense pain. In case of overdosage, fatal respiratory depressions which cannot be treated with nalorphine could be the most severe consequence.

In addition, it has been left out of consideration until now, that an oral depot preparation which became damaged and thus does not retard buprenorphine, but releases it at one blow (called "dosedumping" among experts) cannot immediately be removed from the human body.

The reservations with respect to forms of administration which release buprenorphine in a retarded manner are avoided by the merits of the transdermal therapeutic systems, since the medicinal agent need not be administered to the human body via cannulae so that it can be applied even by nonprofessionals. At the same time, active substance supply according to order is safeguarded; the supply may be interrupted at any time by tearing the system off. Thus, transdermal therapeutic systems seem to be the most suitable form to administer buprenorphine.

However, one has to consider the objection that buprenorphine only badly penetrates through the human skin. This is due to its high molecular weight (m.w. 468) and —above all—its high melting point and very slight solubility in conventional organic solvents and water, and diffusion which is the precondition for penetration through human skin requires dissolved substances.

On the other hand, the solubility must not be increased by salt formation, since bases in ionized form are not absorbed. Until today, all attempts failed to bring buprenorphine on a transdermal basis to a resorption in the required amount, although—for the reasons described above—a TTS is the most suitable form of administration for this active substance.

It is accordingly the object of the present invention to provide buprenorphine or one of the pharmaceutically compatible salts thereof in the form of a transdermal therapeutic system which releases buprenorphine or the pharmaceutically acceptable salt thereof over a period of at least 24 hours in a controlled manner and ensures that the buprenorphine does not notably decompose when the prefabricated transdermal therapeutic system is stored, and which further ensures that buprenorphine, which insufficiently passes through skin, in vivo penetrates through the skin at the required amount.

According to the present invention this object is achieved in a surprising manner by a transdermal therapeutic system for the administration of buprenorphine to the skin. The system comprises a backing layer which is impermeable to the active substance, a pressure-sensitive adhesive reservoir layer, and, optionally, a removable protective layer, and is characterized in that the reservoir layer comprises 20 to 90%-wt polymeric material, 0.1 to 30%-wt softener, 0.1 to 20%-wt buprenorphine base or one of the pharmaceutically acceptable salts thereof, and 0.1 to 30%-wt solvent for the active substance base.

This solution is surprising all the more since buprenorphine has a bioavailability of only 50% when administered sublingually. Since the first liver passage is evaded by this mode of application, the low bioavailability can only be due to insufficient absorbability of the substance by the oral mucosa. However, a substance which only hardly passes the mucosa of the mouth, will be absorbed by the human skin even harder.

The backing layer which is impermeable to the active substance may consist of flexible or inflexible material. Substances suitable for the production of the backing layer are polymeric foils and metal foils, such as aluminum foil which may be used alone or coated with a polymeric substrate. Textile fabrics may be used too, if the components of the reservoir cannot penetrate the fabric due to their physical properties. In a preferred embodiment of the present invention the backing layer is a composite material of an aluminized foil.

The reservoir layer consists of a polymeric matrix and the active substance, whereby the polymeric matrix ensures the coherence of the system. The polymeric matrix consists of a basic polymer and, optionally, conventional additives. The selection of the basic polymer depends on the chemical and physical properties of the buprenorphine. Examples of polymers are rubber, rubber-like synthetic homo-, co- or blockpolymers, polyacrylic esters and the copolymers thereof, polyurethanes and silicones. In principle all polymers are suitable which can be used in the production of pressure-sensitive adhesives and which are physiologically acceptable. Particularly preferred are those consisting of block copolymers based on styrene and 1,3-dienes, polyisobutylenes, polymers based on acrylate and/or methacrylate.

Amongst the blockcopolymers based on styrene and 1,3-dienes, linear styrene-isoprene-blockcopolymers of styrene-butadiene-blockcopolymers are particularly used.

Self cross-linking acrylate copolymers of 2-ethyl hexyl acrylate, vinyl acetate, and acrylic acid with titanium chelate ester, or non-self-cross-linking acrylate copolymers without titanium chelate ester are preferred for the use as acrylate-based polymers.

Suitable polymers which are added to the basic polymer are polymethacrylates, esters of hydrogenated colophony, and polyvinyls.

Copolymers based on dimethylaminoethyl methacrylates and on neutral methacrylic esters are preferably used as methacrylates. The methylesters and glycerol esters of hydrogenated colophony are particularly preferred for the use as esters of hydrogenated colophony. Polyvinylpyrrolidones and polyvinyl alcohols are preferably used as polyvinyls.

The kind of common additives depends on the polymer used: According to their function they can be divided, e.g., in tackifiers, stabilizers, carrier substances, and fillers. The physiologically acceptable substances suitable for this purpose are known to the skilled artisan.

According to the present invention it turned out that a softening agent combined with a solvent for buprenorphine is required to permit transdermal application of buprenorphine.

The choice of softener depends on the polymer. Higher alcohols, such as dodecanol, undecanol, octanol, the esters of carboxylic acids wherein the alcohol component may also be a polyethoxylated alcohol, diesters of dicarboxylic acids, such as di-n-butyladipate, and triglycerides, particularly medium-chain triglycerides of the caprylic/capric acids or coconut oil, have proved to be particularly suitable. Further examples of suitable softeners are multivalent alcohols, for example, glycerol and 1,2-propanediol, which can also be etherified by polyethylene glycols.

The significance of the buprenorphine solvent is proved by the examples. The examples show that the solvent is an indispensable component of the formulation. The combination softener/solvent according to the teaching of the present invention builds the pre-condition for the penetration of the buprenorphine base through the skin.

Suitable solvents for buprenorphine within the matrix are those with at least one acidic group. Particularly suitable are the monoesters of dicarboxylic acids. such as monomethyl glutarate and monomethyl adipate. In principle all acids are suitable which dissolve buprenorphine to a sufficient extent thereby avoiding complete salt formation. In the latter case, penetration through the skin can no longer be expected.

Permanent contact to the skin is ensured by a sufficient self-adhesiveness of the reservoir layer.

The removable protective layer which is in contact with the reservoir layer and removed prior to application, for example, consists of the same materials as used for the production of the backing layer provided that they are rendered removable, for example, by a silicone treatment. Other removable protective layers, for example, are polytetrafluoroethylene, treated paper, cellophane, polyvinyl chloride, and the like. If the laminate according to the present invention is divided into formats suitable for the therapeutical purpose (plasters) prior to application, the dimensions of the protective layers to be applied thereto may have a projecting end with the help of which the protective layer can be removed from the plaster more easily.

The transdermal therapeutic system according to the present invention is produced by mixing homogeneously the active substance together with the components of the pressure-sensitive adhesive reservoir layer, optionally in solution, and spreading it on the backing layer, which is impermeable to the active substance, whereupon the solvent/s is/are removed, if necessary. Subsequently, the adhesive layer is provided with an adequate protective layer.

In principle, the reverse way is possible too, i.e., that the adhesive solution is spread on the protective layer. The solvents are removed too, and it is covered with the backing layer.

The invention is illustrated by the following examples:

EXAMPLE I 10.0 g each of glutaric acid monomethyl ester, methanol, and butanone, and 15.0 g 1-dodecanol are mixed under stirring. Subsequently, 10.0 g buprenorphine base are added; it is stirred until the solid substance is completely dissolved (approximately 30 min., visual control). Then 133.0 g of a self cross-linking acrylate copolymer of 2-ethyl hexyl acrylate, vinyl acetate, and acrylic acid 46% in a solvent mixture (ethyl acetate:heptane:isopropanol:toluene:acetylacetone 37:26:26:4:1) are added under stirring; homogenization follows. Subsequently, 1.3 g aluminum acetylacetonate are additionally added, and it is stirred at room temperature for 3 hours. The evaporation loss is compensated.

189.3 g 52.8%-wt of active substance-containing adhesive solution are obtained which is spread on an aluminized and siliconized polyethylene foil by means of a 350 μm coating bar. After the solvents have been removed by drying to 60° C. for 30 min., the adhesive film is covered with a polyester foil of 15 μm thickness. An area of 16 cm² is punched by means of suitable cutting tools, the edges are separated off. The release of this example and that of the other examples are shown in the table. The table shows both the controlled release into physiological saline and through excited rodent skin.

All further examples are carried out according to the pattern given in Example I. At first the liquid components are mixed, then the buprenorphine base is added. After dissolution of the buprenorphine base, optionally a methacrylate copolymer based on dimethylaminoethyl methacrylate and neutral methacrylic esters is added, and, after dissolution thereof, the adhesive solution is added. The following table shows the components of the formulation after drying. Their meanings are as follows:

Acrylate: Acrylate copolymer of 2-ethyl hexyl acrylate, vinyl acetate and acrylic acid
Semi-ester: Monomethylester of glutaric acid (indicated by G) or adipic acid (indicated by A)
G.L.: Polyethoxylated glycerol with $C_8/C_{10}$-ethoxy groups
polymeric additives: b: copolymer with basic character based on dimethylaminoethyl methacrylate and neutral methacrylic esters; n: copolymer with neutral character based on methacrylic methylester and methacrylic butyl ester; PVP: polyvinylpyrrolidone The in-vitro-release was determined in a shaking-water-bath at 37° C. The acceptor medium was 100 ml physiological saline which was completely renewed after 2, 4, and 8 hours. The concentration was determined by HPLC after 2, 4, and 24 hours. The penetration through the mice skin was measured on the basis of Franz' diffusion cells.

BRIEF DESCRIPTION OF DRAWINGS

FIGS. 1, 2 and 3 illustrate release curves of buprenorphine.

The release curves according to Example 1 are illustrated in FIG. 1 and 2.

INTERPRETATION OF THE IN-VITRO-RESULTS

Examples VII, XIV, and XVII prove the necessity of incorporating into the transdermal systems a solubilizer with at least one acidic group, since the in-vitro-penetration apparently decreases drastically, if such a solubilizer is not present. In these examples the in-vitro-penetration amounts to 0.1 mg/2.54 cm²×h. At the same time, Examples I and XXI demonstrate that it is nearly of no importance whether glutaric acid-or adipic acid monomethylester is used. Example XII proves that a softener has to be added to the solubilizer, since in the absence of a softener the in-vitro-penetration amounts to 0.22 mg/2.54 cm²×24 h, and thus is only slightly above the system without solubilizer.

Examples XIV, VIII, XX, and XVIII serve to examine the influence of the quantity of the semi-esters on the in-vitro-penetration; the semi-ester portion was increased (succession of Examples as stated above) from 0% over 2.5% and 5% to 10%. Due to this, the in-vitro-penetration at the mice skin increased from 0.1 over 0.48 and 0.64 to 0.84 mg/2.54 cm²×24 h. When semi-esters are added, the increase of the in-vitro-penetration is nearly linear. This is illustrated by the following FIG. 3.

The comparison of Examples X and XI shows that 1-dodecanol is preferably used as softener. The other Examples show the influence of the polymeric additives on the in-vitro-penetration—the use of these substances is necessary to ensure film formation, adhesiveness, adherence, and coherence.

It is understood that the specification and examples are illustrative but not limitative of the present invention and that other embodiments within the spirit and scope of the invention will suggest themselves to those skilled in the art.

We claim:

1. A transdermal therapuetic system for the administration of buprenorphine to the skin comprising a backing layer which is impermeable to the active substance, a pressure-sensitive adhesive reservoir layer, and optionally a removable protective layer, the reservoir layer by weight comprising 20 to 90% of a polymeric matrix, 0.1 to 30% of a softening agent, 0.1 to 20% of

| Example | Acrylate | Buprenorphine | Semi-ester | Softener | | Polymeric additive | Release [mg/16 cm² × 24 h] | Penetration of mice skin [mg/2.54 cm² 24 h] |
|---|---|---|---|---|---|---|---|---|
| I | 65% | 10% | 10% G | 1-dodecanol | 15% | — | 16.0 = 74.6% | 0.95 |
| II | 65% | 10% | 10% G | G.L. | 10% | 5% b | 13.6 = 68% | 0.57 |
| III | 60% | 10% | 10% G | 1-dodecanol | 10% | 10% b | 17.0 = 85% | 0.47 |
| IV | 60% | 10% | 10% G | G.L. | 10% | 10% n | — | 0.92 |
| V | 50% | 10% | 10% G | G.L. | 10% | 20% n | — | 0.71 |
| VI | 40% | 10% | 10% G | G.L. | 20% | 20% n | — | 0.56 |
| VII | 50% | 10% | — | G.L. | 20% | 20% n | — | 0.09 |
| VIII | 80% | 10% | 5% G | G.L. | 5% | — | — | 0.28 |
| IX | 67.5% | 10% | 10% G | G.L. | 10% | PVP 2.5% | — | 0.78 |
| X | 65% | 10% | 10% G | G.L. | 10% | 5% b | — | 0.44 |
| XI | 65% | 10% | 10% G | 1-dodecanol | 10% | 5% b | 14.6 = 77.3% | 0.81 |
| XII | 75% | 10% | 10% G | — | | 5% b | 0.22 | |
| XIII | 70% | 10% | 2.5% G | 1-dodecanol | 17.5% | — | — | 0.48 |
| XIV | 80% | 10% | — | 1-dodecanol | 10% | — | — | 0.11 |
| XV | 72.5% | 10% | 2.5% G | 1-dodecanol | 10% | 5% b | — | 0.51 |
| XVI | 65% | 10% | 5% G | 1-dodecanol | 15% | 5% b | — | 0.4 |
| XVII | 65% | 10% | — | 1-dodecanol | 20% | 5% b | — | 0.1 |
| XVIII | 70% | 10% | 10% G | 1-dodecanol | 10% | — | 13.6 = 65% | 0.84 |
| XIX | 60% | 10% | 10% G | 1-dodecanol | 10% | 10% n | 15.3 = 68% | 0.94 |
| XX | 70% | 10% | 5% G | 1-dodecanol | 15% | — | 14.6 = 68.6% | 0.64 |
| XXI | 65% | 10% | 10% A | 1-dodecanol | 15% | — | 16.5 = 73.1% | 0.85 | buprenorphine base or of a pharmaceutically acceptable salt thereof and 0.1 to 30% of a solvent for the buprenorphine or salt thereof.

2. The transdermal therapeutic system according to claim 1, wherein the backing layer is composed of a flexible material.

3. The transdermal therapeutic system according to claim 1, wherein the backing layer is composed of a inflexible material.

4. The transdermal therapeutic system according to claim 1, wherein the backing layer is an aluminum foil.

5. The transdermal therapeutic system according to claim 1, wherein the polymeric matrix is at least one of rubber, a rubber-like synthetic homo-, co- or block-polymer, a urethane and silicone.

6. The transdermal therapeutic system according to claim 1, wherein the softening agent is at least one of dodecanol, undecanol, octanol, a glycol and glycanol.

7. The transdermal therapeutic system according to claim 1, wherein the solvent is a monoester of a dicarboxylic acid.

8. The transdermal therapeutic system according to claim 1, wherein the solvent is at least one of monomethyl glutarate and monomethyl adipate.

9. The transdermal therapeutic system according to claim 4, wherein the polymer is a copolymer of 2-ethylhexyl acrylate, vinyl acetate and acrylic acid, the softening agent is dodecanol and the solvent is monomethyl glutarate.

10. The transdermal therapeutic system according to claim 1, wherein by weight the polymer is present in about 55%, the buprenorphine in about 10%, the solvent in about 10% and the softener in about 15%.

11. A transdermal therapeutic system according to claim 1, wherein the solvent is present in from about 25 to 100% the weight of the buprenorphine.

12. The transdermal therapeutic system according to claim 1, which also comprises a removable protective layer.

13. The transdermal therapeutic system according to claim 1, wherein the pressure-sensitive adhesive reservoir layer comprises a polymer based on an acrylate, a methacrylate or a combination thereof.

14. The transdermal therapeutic system according to claim 1, wherein the softening ester is a medium-chain triglyceride of the caprylic/capric acids of coconut oil.

15. The transdermal therapeutic system according to claim 1, wherein the solvent has at least one acidic group.

16. A laminated composite for administering buprenorphine or a pharmaceutically acceptable salt thereof to an individual transdermally comprising
   (a) a polymer backing layer that is substantially impermeable to buprenorphine or the pharmaceutically acceptable salt thereof; and
   (b) a reservoir layer comprising an acrylate pressure-sensitive adhesive, 0.1 to 20% of buprenorphine base or of a pharmaceutically acceptable salt thereof, 0.1 to 30% of an ester of a carboxylic acid acting as a softening agent and 0.1 to 30% of a solvent for buprenorphine having at least one acidic group.

17. A liminated composite for administering buprenorphine or a pharmaceutically acceptable salt thereof to an individual transdermally comprising
   (a) a polymer backing layer that is substantially impermeable to buprenorphine or the pharmaceutically acceptable salt thereof; and
   (b) a reservoir layer comprising an acrylate pressure-sensitive adhesive, 0.1 to 20% of buprenorphine base or of a pharmaceutically acceptable salt thereof, 0.1 to 30% of an ester of a carboxylic acid acting as a softening agent and 0.1 to 30% of a solvent for buprenorphine having at least one acidic group, wherein the skin contact area of the composite is 16 $cm^2$ and the rate of administration from the composite is about 40 μg/hr.

18. The transdermal therapeutic system according to claim 1, wherein the softening agent is an ester of a carboxylic acid.

* * * * *

UNITED STATES PATENT AND TRADEMARK OFFICE
CERTIFICATE OF CORRECTION

PATENT NO. : 5,240,711
DATED : August 31, 1993
INVENTOR(S) : Hille, et al.

It is certified that error appears in the above-identified patent and that said Letters Patent is hereby corrected as shown below:

Col. 8, line 4    Delete " ester " and substitute -- agent --

Col. 8, line 23   Delete " liminated " and substitute -- -laminated --

Signed and Sealed this

Twenty-ninth Day of November, 1994

Attest:

BRUCE LEHMAN

Attesting Officer    Commissioner of Patents and Trademarks